(12) United States Patent
Bertschinger et al.

(10) Patent No.: US 7,527,954 B2
(45) Date of Patent: May 5, 2009

(54) METHOD FOR IN VITRO EVOLUTION OF POLYPEPTIDES

(75) Inventors: Julian Bertschinger, Zürich (CH); Christian Heinis, Aarberg (CH)

(73) Assignee: ETH Zurich, Zürich (CH)

( * ) Notice: Subject to any disclaimer, the term of this patent is extended or adjusted under 35 U.S.C. 154(b) by 0 days.

(21) Appl. No.: 10/574,227

(22) PCT Filed: Oct. 1, 2004

(86) PCT No.: PCT/CH2004/000610

§ 371 (c)(1),
(2), (4) Date: Apr. 21, 2006

(87) PCT Pub. No.: WO2005/030957

PCT Pub. Date: Apr. 7, 2005

(65) Prior Publication Data

US 2007/0105117 A1    May 10, 2007

(30) Foreign Application Priority Data

Oct. 1, 2003  (CH) .................................... 1671/03

(51) Int. Cl.
*C12Q 1/68* (2006.01)
*C07K 14/00* (2006.01)
*C07H 21/00* (2006.01)
*A61K 38/00* (2006.01)

(52) U.S. Cl. ............................ 435/193; 435/6; 514/2; 536/23.1

(58) Field of Classification Search ...................... None
See application file for complete search history.

(56) References Cited

U.S. PATENT DOCUMENTS 5,856,090 A * 1/1999 Epstein ........................... 435/6

OTHER PUBLICATIONS

Nemoto et al.,"In vitro virus: bonding of mRNA bearing puromycin at the 3'-terminal end to the C-terminal end of its encoded protein on the ribosome in vitro", FEBS Letters 414: 405-408 (1997).*
Doi and Yanagawa, FEBS Lett. 457(2): 227-230 (1999).*
Bertschinger and Neri, "Covalent DNA display as a novel tool for directed evolution of proteins in vitro", Protein Engineering, Design & Selection vol. 17, No. 9, pp. 699-707 (2004).*
Yonezawa, M., et al., "DNA display for in vitro selection of diverse peptide libraries", *Nucleic Acid Research*, vol. 31, No. 19, e118, pp. 1-5, (2003).

* cited by examiner

*Primary Examiner*—Anand U Desai
(74) *Attorney, Agent, or Firm*—The Nath Law Group; Joshua B. Goldberg; Tanya E. Harkins

(57) ABSTRACT

The invention relates to a method for the production and allocation of nucleic acids and polypeptides coded thereby. The method can be used for evolutionary selection of polypeptides in vitro. The inventive method makes it possible to allocate nucleic acids to the polypeptides coded thereby and to select and isolate nucleic acids coding for polypeptides with selected properties. The invention is directed to the use of (cytosin-5)-methyl transferases and to the use of fusion polypeptides or nucleic acid fusion polypeptide complexes covalently bonded thereto according to the inventive method.

18 Claims, 5 Drawing Sheets

SEQUENCE LISTING

<160> NUMBER OF SEQ ID NOS: 7

<210> SEQ ID NO 1
<211> LENGTH: 24
<212> TYPE: DNA
<213> ORGANISM: Artificial
<220> FEATURE:
<223> OTHER INFORMATION: PCR primer -continued

<400> SEQUENCE: 1
gatgccggcc acgatgcgtc cggc                                          24

<210> SEQ ID NO 2
<211> LENGTH: 40
<212> TYPE: DNA
<213> ORGANISM: Artificial
<220> FEATURE:
<223> OTHER INFORMATION: PCR primer, the cytidine in position 9 was
      replaced by 5'-fluorodeoxycytidine

<400> SEQUENCE: 2
cgtcatggcc tatgcgggcg accacacccg tcctgtggat                          40

<210> SEQ ID NO 3
<211> LENGTH: 24
<212> TYPE: DNA
<213> ORGANISM: Artificial
<220> FEATURE:
<223> OTHER INFORMATION: double-stranded fragment for blocking magnetic
      beads, labelled with biotin on 5' end, obtained from the company
      Qiagen

<400> SEQUENCE: 3
ggagcttctg cattctgtgt gctg                                          24

<210> SEQ ID NO 4
<211> LENGTH: 81
<212> TYPE: DNA
<213> ORGANISM: Artificial
<220> FEATURE:
<223> OTHER INFORMATION: competing double-stranded DNA fragment,
      obtained from the company Qiagen

<400> SEQUENCE: 4
atctaaggcc aatgtactag acggccattc cagatgcagg ccaagcgtac atacggccta    60
gctaaatcaa ggccgtatcg t                                             81

<210> SEQ ID NO 5
<211> LENGTH: 23
<212> TYPE: PRT
<213> ORGANISM: Artificial
<220> FEATURE:
<223> OTHER INFORMATION: calmodulin-binding peptide, labelled with
      biotin on amino-terminus

<400> SEQUENCE: 5

Cys Ala Ala Ala Arg Trp Lys Lys Ala Phe Ile Ala Val Ser Ala Ala
1               5                   10                  15

Asn Arg Phe Lys Lys Ile Ser
            20

<210> SEQ ID NO 6
<211> LENGTH: 22
<212> TYPE: DNA
<213> ORGANISM: Artificial
<220> FEATURE:
<223> OTHER INFORMATION: PCR primer

<400> SEQUENCE: 6
cccgcgaaat taatacgact ca                                            22

<210> SEQ ID NO 7
<211> LENGTH: 20
<212> TYPE: DNA

-continued

```
<213> ORGANISM: Artificial
<220> FEATURE:
<223> OTHER INFORMATION: PCR primer

<400> SEQUENCE: 7
aaaacccctc aagacccgtt                                               20
```

METHOD FOR IN VITRO EVOLUTION OF POLYPEPTIDES

The present invention relates to a method for the production and allocation of nucleic acids and the polypeptides coded by these that can be used for the evolutionary selection of polypeptides in vitro. The method according to the invention does not only allow for the allocation of nucleic acids to the polypeptides coded by these, but, furthermore, also for the selection and isolation of nucleic acids, that code for polypeptides with selected properties. Moreover, the invention is directed to the use of (cytosine-5) methyl transferases and to the use of fusion polypeptides or covalently bonded nucleic acid-fusion polypeptide complexes in the method according to the invention.

The production of polypeptides with selected properties (specific binding properties, specific properties such as, e.g., catalysis, activation or inhibition of biological activities) is of great economical interest. Polypeptides with said properties must be identified and selected from a very large number of polypeptide variants. Ultimately, such a process is an imitation of the natural evolution. Typically, a large number of genetically diverse polypeptide mutants are produced in a first step. In a second step these polypeptide mutants are selected according to desired properties. This process for the production of diversity and subsequent targeted selection can be repeated as often as it is desired. However, one must be able to allocate the genetic information (genotype) to the polypeptide (phenotype), which is mostly done by physically bonding one to the other.

At present, a number of methods for the selection of nucleic acids coding for polypeptides are known. These methods employ different strategies for physically joining the genotype and phenotype of a polypeptide library.

The technique that is called "phage display" is successfully employed for the selection of polypeptides having specific binding properties (review in Clackson T. and Wells J. A. (1994) In vitro selection from protein and peptide libraries. *Trends Biotechnol.* 12(5): 173-84). In this method filamentous phage particles carry the polypeptide on their surface and the genetic information (genotype) on the inside. The physical connection between the nucleic acid (DNA) and the gene product (protein) takes place during the production of the phage particle on the inside of bacterial cells. For doing so similar technologies are known, wherein the carrier of the phenotype and genotype are yeast cells (yeast display) or bacterial cells (bacterial cell display) instead of phage particles. These techniques have in common that the DNA molecules coding for the polypeptide variants are incorporated into cells for the production of polypeptide libraries. However, the production of large amounts of circular DNA and their transformation in cells is very laborious. Furthermore, the size of the peptide libraries is limited. Libraries having $10^{11}$ polypeptide variants were only produced with great effort. Libraries having $10^8$ to $10^9$ polypeptide variants are routinely cloned.

In another method for the evolutionary selection of polypeptides the polypeptides to be selected are bonded to the coding nucleic acids by fusion to a DNA-binding protein, the Lac repressor (Cull M. G. et al. (1992) Screening for receptor ligands using large libraries of peptides linked to the C terminus of the lac repressor. *Proc. Natl. Acad. Sci.* U S A. 89(5): 1865-9). The repressor protein binds the polypeptide to the coding plasmids by non-covalent bonds to a Lac operator sequence on the plasmid. In order to ensure that the polypeptide binds to the nucleic acid coding it, the reaction takes place on the inside of bacterial cells. Because of the in vivo binding of the genotype and phenotype the size of the polypeptide library is also limited in this technology, because the production of large amounts of circular DNA and the transformation thereof in cells is very laborious. In this technique the employed non-covalent bond of the nucleic acids to the polypeptides requires very mild reaction conditions during the subsequent selection process. Therefore, polypeptides having very strong binding properties (long living complexes with slow dissociation kinetics (low $k_{off}$) cannot be selected due to the non-covalent bond, because the nucleic acid and the polypeptide would dissociate during the long incubation periods required for these selections.

In the so-called "ribosome display" (or also polysome display) method polypeptides are bonded to the surface of ribosomes together with the nucleic acids coding for said polypeptides (Roberts R. W. (1999) Totally in vitro protein selection using mRNA-protein fusions and ribosome display. *Curr. Opin. Chem. Biol.* 3(3): 268-73). The bond is formed when the translation of the ribonucleic acid is halted. The polypeptide being formed remains bonded to the ribosome together with the coding mRNA. With this method polypeptides specifically binding to different target polypeptides (e.g. peptides, antibodies or ankyrines) were isolated. This method has the advantage that it takes place completely in vitro, whereby larger polypeptide libraries ($>10^{12}$) can be prepared. A disadvantage of the ribosome display technology is the necessity of performing the selection of the polypeptides under specific conditions (high salt concentration, low temperature), whereat the RNA/ribosome/polypeptide complexes are stable, but that do not necessarily also correspond to the conditions of the method used for the polypeptide selection.

In another method for connecting the phenotype and genotype the mRNA is at first covalently bonded to puromycin, that is subsequently bonded to the mRNA-encoded polypeptide. In the so-called "in vitro virus" method the mRNA that carries a puromycin group at the 3'-end is translated. When the ribosome reaches the end of the coding region (open reading frame) of the mRNA the puromycin group is covalently bonded to the polypeptide being formed. A further disadvantage of this method is that the genotype is coded by mRNA. A mRNA can be degraded enzymatically by very small RNAse contaminations. Various methods related to the "in vitro virus" method are known, wherein the RNA is substituted for more stable DNA by laborious methods (Roberts R. W. and Szostak J. W. (1997) RNA-peptide fusions for the in vitro selection of peptides and proteins. Proc. Natl. Acad. U S A. (94(23): 12297-302; U.S. Pat. No. 6,281,344: Nucleic acid-protein fusion molecules and libraries.

In addition, a method for the in vitro connection of the phenotype and genotype was suggested, that is based in the nicking property of the replication initiator of the *E. coli* bacteriophage P2A (FitzGerald, K. (1999) In vitro display technologies—new tools for drug discovery. (*Drug Discovery Today*, Vol. 5, No. 6). The replication initiator is an endonuclease that breaks up one strand of the DNA and that is bonded covalently to the 5'-end of the DNA by a tyrosine group while doing so. Because the translation already takes place during transcription in the bacterial production of proteins the newly formed P2A polypeptide fusion protein comes into contact with its coding DNA. This cis activity of the enzyme is supposed to allow for the coupling of genotype and phenotype in vitro. However, there are no proteins known, whose properties have been improved by this method.

A further known method for the in vitro bonding of phenotype and genotype is based on the non-covalent but high affinity binding of mRNA-aptameres to Tat-proteins of HIV1

(Fujita S. et al. (2002) Novel approach for linking genotype to phenotype in vitro by exploiting an extremely strong interaction between RNA and protein. J. Med. Chem. 45(8): 1598-606). The connection of genotype and phenotype take place in vitro during translation the same as in the "ribosome display" and the "in vitro virus" methods. This method has the disadvantage that there is the risk that the components dissociate. Moreover, the method is based on mRNA for coding the genotype that is susceptible to RNAse degradation.

A similar method is based on the binding of streptavidin-polypeptide conjugates to the biotinylated nucleic acid encoding these in microcompartments (Doi N. and Yanagawa H. (1999) STABLE: protein-DNA fusion system for screening of combinatorial protein libraries in vitro. FEBS Lett. 457(2): 227-30). To ensure the cis conjugation of genotype and phenotype the streptavidin-polypeptide conjugates are transcribed and translated in this method in aqueous compartments in a water-in-oil emulsion. Each compartment contains at most one nucleic acid. After the translation of the streptavidin-polypeptide conjugates these can bind to the biotinylated DNA in the compartment. The polypeptide-nucleic acid conjugates may subsequently be extracted from the emulsion and be subjected to a selection method based on the desired properties. However, a limitation of this method is the inefficient expression of streptavidin in the transcription-/translation mixture.

Further methods for coupling genotype and phenotype are known that are also based on the compartmentalisation of DNA together with a transcription-/translation mixture in a water-in-oil emulsion (Sepp A. et al. (2002) Microbead display by in vitro compartmentalisation: selection for binding using flow cytometry. FEBS Lett. 532(3): 455 -8; U.S. Pat. No. 6,489,103: In vitro sorting method). In such a method beads were employed as carrier of the genotype and phenotype. On each bead a coding DNA fragment and a plurality of peptide sequence-specific antibodies were attached. The DNA fragment carries the genetic information for a peptide sequence, that is fused to a variable polypeptide. The beads are encapsulated in separate compartments of a water-in-oil emulsion together with a transcription-/translation mixture. The expressed polypeptide-peptide conjugates are immobilised by binding to the antibodies on the beads. This method has the disadvantage that also in this method genotype and phenotype can dissociate under the conditions of the selection method. Because of this, there is the risk of an exchange of polypeptide-peptide conjugates between different beads and as a result there is the risk of a wrong allocation of genotype to phenotype.

In another method for coupling genotype and phenotype in vivo methylase-polypeptide-fusion polypeptides are bonded to DNA (U.S. Pat. No. 5,856,090: DNA-methylase linking reaction). The DNA contains the methylase recognition sequence 5'-GGCC-3', wherein the third base (cytidine) is replaced by fluorodeoxycytidine (F). The new sequence 5'-GGFC-3' serves as a suicide inhibitor (also called a "mechanism-based inhibitor"). Methylase-polypeptide fusion proteins reacting with this sequence remain irreversibly bound to the DNA. For doing so, circular DNA that contains the sequence 5'-GGCC-3' and at the same time the gene for a methylase polypeptide is introduced into bacterial cells. Fluorodeoxycytidine is added to the culture medium of these cells that in incorporated into the 5'-GGCC-3' sequence during the replication of the plasmid. Methylase-polypeptide fusion proteins can bind covalently to the plasmid. This method has the disadvantage that the number of methylase fusion proteins that are bound to a plasmid cannot be defined exactly. Well expressed polypeptide mutants are immobilised more abundantly on the plasmid, which in turn leads to the fact that a well expressed polypeptide mutant having average binding properties may be superior to a less expressed but very well binding polypeptide mutant in the selection process due to avidity effects. Moreover, in this technology the size of the polypeptide library is also limited due to the in vivo binding of genotype and phenotype.

The international patent application WO 98/37186 discloses a method for the production of a protein expression library, wherein the proteins are covalently bonded to the DNA encoding these. The protein conjugates used code for a protein-DNA binding region (protein A of phage P2; P2A) and a display region (the protein to be assessed).

However, one takes from the document of Liu Y. and Haggard-Ljungquist E., *Nucleic Acid Research*, 22, p. 5204-5210 (1994) that is mentioned in the summary of the above mentioned patent application that the purified protein A of the phage P2 used for covalently binding the DNA does not bind to double-stranded ori-containing DNA, but only to single-stranded ori-containing DNA, thereby pointing out that a special DNA structure and/or a specific protein is necessary to make the ori accessible for the protein A. This limitation was also observed for other proteins with the same function. In the experimental section of this document it is concretely noted that protein A forms inclusion bodies and that no soluble protein is detectable. Therefore, this protein must be denatured at first and subsequently be folded in vitro. Because of this the expression of this protein in functional form is very inefficient.

The above mentioned WO 98/37186 also points out that P2A needs to be activated by ssDNA first. The system described here was so inefficient that the same applicant (Isogenica) recognized the previous application in a later application (WO 04 022 746) as follows:

"Another prior art method, covalent display technology, or CDT, is described in WO 98/37186. This method relies on covalent linkage of protein to DNA to retain the linkage of genotype to phenotype, through the cis action of the crosslinking protein. This method teaches that two requirements are needed for successful use of this technique. Firstly, proteins are required which interact in vitro with the DNA sequence which encodes them (cis action), and secondly, said proteins must establish a covalent linkage to their own DNA template. This method suffers form the fact that the DNA is chemically modified which can prevent the recovery and identification of the binding peptide of interest.

There remains a need for more versatile in vitro methods of constructing peptide libraries in addition to the methods described above, which can allow direct selection of binding activity, as well as for enzymatic activity, and that allow efficient production of complex peptide structures, whole still allowing recovery of intact genetic material encoding the peptide of interest."

It is therefore noted that a covalent bonding of genotype and phenotype had no practical utility due to defects of the system.

For a binding of polypeptides to the DNA coding them it is to be observed that the binding to the DNA is specific and that a defined number of polypeptide molecules is bound per DNA molecule. The latter is important because in selection methods the number of polypeptides that are bound to a DNA molecule may be critical for the success of the experiment. If, for example, specifically binding proteins are selected, an avidity effect can lead to the result that polypeptides having a lower affinity can be selected, because several polypeptides are bound to a DNA molecule. This is only rarely desirable when it is difficult to obtain any proteins at all for binding a specific protein. In this case one tries to select binding proteins having a lower affinity in order to subsequently produce high affinity proteins starting from these. The selection of antibodies with the phage display technology has demonstrated that it is very difficult to select antibodies with high affinity, when more than one antibody is located on the phage surface (Winter G. et al. (1994) Making antibodies by phage display technology. *Ann. Rev. Immunol.* 12: 433-55).

Therefore, it is the object of the present invention to provide a method that does not have the disadvantages of the state of the art. In particular, it is desired in such a method that the number of polypeptides that are bound per DNA molecule can be controlled. For example, an avidity effect can be avoided in this way. The method should be faster and more efficient, e.g. have short incubation periods and avoid time-consuming cell cycles. It is a further object to provide a bond between genotype and phenotype, that is sufficiently robust to perform selection, methods with a lot of and often rough conditions, too.

Furthermore, the present invention is based on the objective to provide a method whereby nucleic acids can be efficiently and rapidly selected in an uncomplicated way according to the properties of the coded proteins. Preferably a nucleic acid cannot only be selected according to the properties of the coded protein by this method but also be optimised in an evolutionary manner by modifying and optimising the nucleic acid in singular or several cycles of the method.

The problems underlying the present invention are solved by the method according to claim 1.

The present invention relates to a method for the production and allocation of nucleic acids and the polypeptides coded by these, comprising the following steps:
  a) the compartmentalisation of nucleic acids together with an in vitro transcription-translation mixture in a water-in-oil emulsion,
  b) the in vitro expression of the fusion polypeptides coded by said nucleic acids in the microcompartments of the water-in-oil emulsion, whereby each nucleic acid is bonded to the fusion polypeptide it codes for,
  wherein each of the fusion polypeptides comprises at least one constant peptide part I and at least one variable peptide part II, and wherein the fusion polypeptides are covalently bonded to the nucleic acid coding for said fusion polypeptide in step b), and wherein the number of the fusion polypeptides per nucleic acid bonded in this manner is a definable integer.

This method allows for the allocation and production of nucleic acids together with the polypeptides coded by these. Such a connection of genotype and phenotype is indispensible for selection methods for large numbers of nucleic acids based on the properties of the proteins coded by these, because, otherwise, each nucleic acid and/or each protein has to be stored and used in a container.

It was surprisingly found that the covalent bond employed in this in vitro method binds the genotype (nucleic acid) and the phenotype (the protein) in a stable manner to each other and allows for an exact control of the ratio of protein to the nucleic acid.

The term "definable integer" as it is used in the context of the present invention means that the nucleic acid sequence or structure defines, i.e. specifies, the exact number of fusion polypeptides binding thereto by the number of recognition sequences for nucleic acid binding proteins.

It is essential for the method of the present invention that the nucleic acid codes for a fusion polypeptide, that comprises at least one constant peptide part I that binds covalently to the nucleic acid coding the fusion peptide, and that comprises at least one variable peptide part II, that is used for selecting the desired nucleic acid in a suitable selection method.

During the selection of the polypeptides the covalent bond between the nucleic acid and the polypeptide ensures the stability of the complex under partially harsh conditions without damaging the bond between the nucleic acid and the polypeptide.

In a preferred embodiment the method additionally comprises the step of extracting the fusion polypeptide-nucleic acid complexes prepared in step b) from the water-in-oil emulsion.

By extracting the fusion polypeptide-nucleic acid complexes from the water-in-oil emulsion the complexes can be prepared for later steps, e.g. selection methods. Also, other purification and/or isolation methods that are known to the skilled person may be practiced.

In a further preferred embodiment the method according to the present invention additionally comprises the step of selecting from those fusion polypeptide-nucleic acid complexes, wherein the peptide fusion part has the desired properties. These properties may be a specific binding to other molecules, e.g. proteins, peptides, metals, polymers, etc. or, also, specific biological functions such as a catalytic effect or the activation or inhibition of other molecules or biological systems, e.g. of cell-free and cell- or even tissue systems. Preferably, the complete method according to the invention is performed in vitro. However, the selection step can also comprise the use of, e.g. cells and tissues.

All methods known in the field for selecting, proteins that may optionally be routinely adapted to the specific needs of the respective DNA-fusion polypeptide complexes are available to the skilled person. It is merely required for these selection methods that neither the fusion polypeptide nor the DNA nor the bond between both of them is affected, i.e. modified or destroyed. Typical screening methods may be employed as selection methods, wherein a plurality of substances is assayed simultaneously and as a whole, but also selection methods, wherein the result is established for each assayed substance (here DNA-protein complexes). As a selection method one or more, the same or different method can be employed in parallel or sequentially. Exemplary embodiments of selection methods are illustrated in the examples.

A further preferred embodiment of the method according to the invention comprises the amplification of the selected nucleic acid molecule optionally after a prior extraction step. By amplifying the selected genotype is again separated from the phenotype. The amplified nucleic acids can now be employed for the production of the coded proteins and peptides or they can also be again introduced into a method according to the invention, e.g. with one or more other selection methods, in order to provide a subselection.

In a more preferred embodiment the method according to the invention additionally comprises the step of random or directed mutation of nucleic acids resulting from the method. For example, by mutation the substitution, deletion, chemical modification or insertion of one or more nucleotide(s) during or after the amplification of step e) is understood. A random or directed mutation allows for again employing the already selected nucleic acid with regard to altered properties in the method of the invention and, thereby, to optimise it by the same or different selection methods. For example, in this manner a nucleic acid, for which its protein product has already been selected as binding specifically, can be further optimised according to the invention. In addition, the skilled person can optimise nucleic acids or their polypeptide products with regard to an activating, inhibiting or catalysing effect using the method of the invention.

In a further preferred embodiment the method according to the invention additionally comprises the step of the repetition of one of the previous methods with the same or a different selection method once or several times for the purpose of optimising the selected nucleic acids, optionally after a single or multiple mutation of the nucleic acids.

Preferably, the nucleic acids employed in the method according to the invention are double-stranded rRNA, mRNA or DNA. More preferably, the nucleic acids are DNA and, most preferred, they are linear DNA, because these can be produced rapidly and easily by polymerase chain reaction.

In a further preferred embodiment the nucleic acids employed in the methods of the invention are chemically modified nucleic acids, in particular, chemically modified DNA. Chemically modified DNA is one that contains other than the common nucleotides and/or additional chemical building blocks that differ from the naturally occurring bases A, T, G and C. For example, such modifications can be useful for the covalent bonding to the constant peptide part I of the coded fusion polypeptide. If the modification cannot be introduced by common amplification, the modification(s) can be introduced, for example, directly before the compartmentalisation step a) or in the amplification step e) by means of accordingly modified primers. Other chemical methods for introducing modifications into nucleic acids are known to the skilled person and may be employed in the present invention.

Preferably each microcompartment of the water-in-oil emulsion, that is employed in the method according to the invention does not comprise more than one nucleic acid. This can ensure that the allocation of a nucleic acid to the polypeptide it codes for, i.e. the binding of both, does not lead to a misinformation in the selection methods.

For microcompartments made from a water-in-oil emulsion such an allocation is most often ensured by those with an average diameter of 1 µm to 2 µm, microcompartiments of this size being preferred embodiments of the present invention.

In the method according to the invention each constant peptide part I is preferably covalently bound to one nucleic acid molecule. This 1:1 ratio avoids avidity effects, precipitation and, in particular, a steric hindrance of the protein part during selection methods, where the selection also depends on the accessability of the regions that mediate the selection.

In a preferred embodiment the constant peptide part I of the fusion polypeptide is a (cytosine-5-)-methyl transferase.

It was surprisingly demonstrated that methyl transferases bind in vitro to nucleic acids with high stability and, moreover, can be easily transcribed and translated in vitro. The DNA bond of these substances also withstands the rough experimental conditions of most of the selection methods for proteins. Its use for linear DNA is surprising, too. Up to now methyl transferases were merely employed in cells in vivo to bind to circular plasmids.

DNA-(cytosine-5-) methylases are found in prokaryotic as well as in eukaryotic organisms. The amino acid sequences of the members of the family of the prokaryotic (cytosine-5-)-methyl transferases have a high degree of homology. This homology is strongest in 10 conserved regions of these proteins. All (cytosine-5-)-methyl transfersaes transfer a methyl group from the cofactor S-adensylmethionine to the position 5 of a cytosine in the DNA.

Preferably, the methyl transferase is selected from the group consisting of M.Hae III, M.Hha I, M.Hpa I, M.Msp I and Alu I.

In the following the above-mentioned methyl transferases and their corresponding recognition sequence are shown.

| M.Hae III | Haemophilus aegypticus | 5'-GGCC-3' |
|---|---|---|
| M.Hha I | Haemophilus heamolyticus | 5'-GCGC-3' |
| M.Hpa I | Haemophilus parainfluenzae | 5'-CCGG-3' |
| M.Msp I | Moraxella species | 5'-CCGG-3' |
| Alu I | Arthrobacter luteus | 5'-AGCT-3' |

Further methylases that are useful for practicing the invention are known to the skilled person or they are easily found (e.g. in the catalogue of *New England Biolabs*, that sells purified enzymes).

However, next to the above-mentioned methylases other proteins or peptides known to the skilled person may be employed according to the invention to bind DNA covalently. Preferably these are terminal proteins.

Proteins binding covalently to DNA are known, for example, from phages of *Streptomyces pneumoniae* and *E. coli* (for example, Phi29, Cp-1 and PRD1). Further such proteins are present in virus, e.g. adenovirus, in linear plasmids (example S1, Kalilo) and also in bacteria (e.g. *Streptomyces*).

The terminal protein (TP) of the bacteriophase phi29 is the best characterized one. It binds to the 5'end of DNA. During replication of the genome of phi29 the end of the newly synthesized DNA strands is bound to the terminal protein (protein priming mechanism). However, for this purpose a quaternary complex of "old TP-DNA", phi29 DNA polymerase and "new" TP is necessary. However, this system is not practical in in vitro expression systems with subsequent direct cross-linking. Meijer, W. J. J., Horcajadas J. A., Salas M., phi29 family of phages, *Microbiology and Molecular Biology Reviews* (2001), p. 261-287.

The methyl transferase Hae III from *Haemophilus aegypticus* is especially preferred for practicing the method according to the invention.

In this context the use of a modified nucleic acid comprising the sequence 5'-GGFC-3', wherein F is 5-fluorodeoxycytidine as a recognition sequence of the methyl transferase is particularly preferred.

A further aspect of the invention relates to the use of preferred reagents for practicing the method of the invention. In this respect, a preferred embodiment is the use of at least one (cytosine-5)-methyl transferase in a method according to the invention.

A further preferred embodiment in this respect is the use of fusion polypeptides or covalently bonded nucleic acid-fusion polypeptide complexes in a method according to the invention, that each comprise at least one constant peptide part I and at least one variable peptide part II, wherein the fusion polypeptides are covalently bonded to the nucleic acid coding said fusion polypeptide by the peptide part I and wherein the number of fusion polypeptides per nucleic acid bonded in this manner is a definable integer.

In the following single method steps of the present invention are illustrated in an exemplary manner with reference to the figures.

In a first step A in Figure A a collection of genes differing slightly from each other 1 (DNA library 1) is enclosed in the aqueous phase of a water-in-oil emulsion 3A together with a suspension that allows for the expression of these genes (transcription-/translation solution). This is preferably done in such a way that at most one nucleic acid (preferably a linear DNA molecule 2) is present per aqueous compartment 3B.

Then, the gene present in the aqueous compartment is expressed as a polypeptide by the components of the transcription-/translation solution.

Fusion polypeptides 5 prepared according to the invention comprise the two peptide parts I and II. The peptide part I 5A is a polypeptide, that can react by itself with a chemical group present on a DNA molecule or the nucleic acid itself. This chemical group (star *, here at the left end of the DNA 2) can either be arranged in the sequence of DNA 2 or be added to one of the ends of the DNA 2. During a chemical reaction a covalent bond and, thereby, a polypeptide-DNA complex 6 is formed between the polypeptide and the DNA molecule. The variable peptide part II 5B is a polypeptide, whose properties are determined according to the selection step of the invention. Finally, an in vitro evolution takes place by the method according to the invention.

Preferably, the DNA-polypeptide fusion complexes 6 are separated from the emulsion by extraction (step B) subsequent to the binding. In this way a collection 4 of DNA-polypeptide complexes 6 is obtained, wherein the DNA molecule 2 is covalently bonded to the polypeptides 5A/5B, wherein each nucleic acid molecule 2 is bonded to the the fusion polypeptide 5, it codes for.

Using this collection 4 of DNA-polypeptide fusion complexes 6 polypeptides with selected, also pre-selected, properties are chosen, screened or selected in a selection method according to the invention. (step C). For example, the selection of specifically binding polypeptides takes place by affinity purification. For this purpose the collection 4 of polypeptide-DNA complexes 6 is added to immobilised target molecule 8, for which a specifically binding polypeptide 7 is to be found. The non-binding polypeptide-DNA complexes are washed away.

Subsequently (step D), the genetic information of the bound polypeptide 7 is amplified by PCR (polymerase chain reaction) and, thereby, is separated from the complex. During amplification a new collection 9 of genes is obtained, which may be used for practicing a further polypeptide-DNA complex- and selection cycle (route E). After a sufficient number of such selection cycles according to the invention the selected DNA fragments can either be mutated for further cycles or be cloned for a closer characterization of the coded polypeptides (route F).

By practicing the method of the invention the evolutionary process, the generation of diversity, the survival of the fittest by selecting advantageous variants, the propagation and generation of new diversity in the test tube is imitated. For example, the advantages over existing technologies comprise:

a) The complete method takes place in vitro, i.e. the transformation of living cells, that is limiting to the size of the library is circumvented.
b) The polypeptide-genotype complex preferably contains no RNA. Therefore, the risk of contamination with RNAase (contrary to other in vitro methods such as ribosome display or mRNA display) is irrelevant.
c) The method according to the invention allows for a simple production of DNA libraries. Because only PCRs need to be conducted, neither a restriction digest nor a ligation or a transformation of cells is necessary. This leads to a strong reduction of the time period necessary for preparing a nucleic acid library (a few days instead of several weeks). Therefore, several selection-/evolutionary cycles can be practiced one after another and with little complexity in a relatively short time period.
d) A covalent bond is formed between the polypeptide (phenotype) and the DNA (genotype) that has the advantage that the stability of the complexes can be ensured, optionally after having performed an extraction of the polypeptide/DNA-fusion complexes from the emulsion.
e) Preferably, only one single fusion polypeptide is bound per nucleic acid molecule. The choice/selection of high affinity binders (monovalent display) is made possible with a minimal avidity effect and an increased sensitivity.

According to the invention a water-in-oil emulsion is used for compartmentalisation according to the invention. For this purpose many small water compartments surrounded by oil are formed, that serve to spatially join a nucleic acid/gene (preferably a DNA molecule) and its genetic products. The compartmentalisation allows for contacting the genotype of the gene with the selected properties of its coded product (RNA or polypeptide), i.e. the phenotype. The spatial allocation and confinement ensures the unambiguous allocation of the covalent bond.

During the production of the water-in-oil emulsion care needs to be taken that the emulsion is stable enough so that the genes/nucleic acids and their genetic products (mRNA and polypeptides) cannot diffuse between compartments so that a misallocation occurs. Also, the water compartments cannot be allowed not fuse to each other. The water-in-oil emulsion is preferably stabilized by the addition of tensides (e.g. Span 80, Tween 80) to the oil phase (e.g. mineral oil). By doing so, a spontaneous separation of the water- and oil phase can be prevented.

In FIG. 2 the processes within the microcompartments or water compartments of a water-in-oil emulsion are illustrated schematically. In each water compartment there preferably is at most one DNA molecule 2 present with, example given, a suicide inhibitor (e.g. a (cytosine-5)-methyl transferase recognition sequence) or a chemical group (star symbol). In a first step (III, transcription) mRNA 10 is synthesized starting from the DNA molecule 2 that is present in the water compartment, which is used as a template for a second step (IV, translation). In this manner the fusion protein or fusion polypeptide 5 (consisting of the domains 5A and 5B) is expressed. This fusion polypeptide 5 reacts with the suicide inhibitor (*) at or on the DNA molecule (step V) and forms a DNA-polypeptide complex 6 (see FIG. 1). This connection of genotype and phenotype allows for the choice/selection of genes by the properties of the phenotype. The subsequent amplification (here polymerase chain reaction, PCR) of the selected genes results in a propagation of the DNA molecules that were determined in the selection method. When a polypeptide now forms a covalent bond with a DNA molecule, that does not code for this polypeptide, then DNA molecules could be selected, that do not code for polypeptides with selected properties. Because of this, it is important for in vitro evolution in the method of the present invention that polypeptides are coupled to their corresponding genes.

The size of the water compartments 3B is very important to ensure on one side the expression of the genes (U.S. Pat. No. 6,489,103 B1, In vitro sorting method) and, on the other side, the binding of the DNA molecules 2 to the expressed fusion polypeptide 5 in an efficient way. The binding efficiency depends on the size of the water compartments, because the binding reaction is a bimolecular process. This means that the speed of the coupling increases with an increase in the concentration of the DNA and the proteins to be coupled.

The concentration of the DNA determines how many molecules of a substance are present per volume unit. In the present invention it is preferred, that at most one DNA molecule is present per water compartment, because preferred genotype-phenotype fusion complexes may be obtained in this way. Because of this, the concentration of DNA is reduced by the third power relative to the increase in the diameter of the water compartments. In this way a DNA molecule in a water compartment with a diameter of 2 μm results in a concentration of 0.4 nM, whereas a DNA molecule in a mirco compartment of 1 μm in diameter will calculate to a concentration of 3.2 nM. The same considerations can be made for the expressed polypeptides. The preferred size (i.e. the preferred diameter) of the water compartments for this invention lies in the range of 1 μm and 2 μm.

With an average diameter of the compartment of 1 μm about $10^{11}$ compartments can be formed in 1 ml emulsion. It is desirable to produce a number of compartments as high as possible, because then one can work with larger DNA libraries. However, the water compartments should not fall short of a certain minimal size because otherwise and according to U.S. Pat. No. 6,489,103 not all molecules will fit that are required for the expression of the polypeptides.

There is a certain tolerance of the methods according to the invention with regard to a false positive selection during the first selection cycle. For example, if more than one DNA fragment arrives at one compartment, it is possible, that a selected phenotype is falsely bound to a non-desired genotype. If the complex is isolated in the subsequent selection, its DNA is propagated by PCR amplification. However, these falsely positive selected genotypes do not pose a problem, because they can be eliminated in the following selection cycles.

For example, the water-in-oil emulsion can be prepared by simple mixing of the aqueous and the organic phase. The mixing can be accomplished with several methods described in the literature (Finch C. A. et al., (1993) Encapsulation and controlled Release. *Spec. Publ.-R. Soc. Chem.* 138, 35). For example, the oil phase can be stirred with a magnetic stirrer, while the aqueous phase is slowly added dropwise. After the addition of the aqueous phase it is typically stirred for a certain time period until the compartments of the emulsion have the desired size distribution. The time period and speed of stirring are very important parameters for the size distribution of the water compartments (Tawfik D. S. and Griffiths A. D. (1998) Man-made cell-like compartments for molecular evolution. *Nat. Biotechnol.* 16(7), 652).

In order that polypeptides can be expressed in a water-in-oil emulsion starting from linear or circular DNA fragments, the machinery for the protein synthesis must be incorporated into the compartments together with the DNA. This machinery consists of a coupled in vitro transcription-/translation system. A number of commercial products are available for this purpose. The cell-free expression of polypeptides in a water-in-oil emulsion was already described in the literature in 1992 (Nametkin S. N. et al. (1992) Cell-free translation in reversed micelles. *FEBS* 309, 330). The yield of polypeptides expressed in a water-in-oil emulsion is typically slightly lower in non-compartmented solution. The extent of the reduction of the yield depends on the expressed polypeptid (U.S. Patent 2002/119459, Optical sorting method).

The polypeptide-DNA complexes can be extracted from the emulsion after the expression of the polypeptides and their coupling to the DNA in the aqueous phase. For this purpose, the emulsion is centrifuged and the water compartments sink to the bottom of the reaction vial. The water compartments form a sediment, but are still intact. The oily supernatant is commonly removed. Now the aqueous phase can be extracted from the oil phase (see Tawfik D. S: and Griffiths A. D., 1998).

Preferably, the actual selection experiment is done with the extracted polypeptide-DNA fusion complexes.

For this purpose the molecule, for which, e.g. a binding polypeptide is sought, can be immobilized on a solid surface. This surface can be the resin of a chromatography column, a plastic surface or small beads. The polypeptide-DNA fusion complexes that can bind to the immobilized molecule still remain on the solid surface when the system is washed. After the washing the remaining polypeptide-DNA fusion complexes may be eluted from the surface and subsequently be amplified by PCR. By using beads the remaining DNA molecules may be amplified, optionally directly after the washing step (no elution). During the amplification one obtains a new selected DNA library. With this either a further complex forming- and selection cycle may be performed or new mutations may be introduced, in order to increase the diversity of the DNA library. Methods for mutageneses are described in the literature and known to the skilled person.

In the following a preferred route for practicing the invention will be illustrated in an exemplary manner:

For the coupling of polypeptide and nucleic acid the protein Hae III methylase from *Haemophilus aegypticus* (M.Hae III) (ATCC 1116) is used. M.Hae III methylates the third base from the left (cytidine, C) in the recognition sequence 5'-GGCC-3'. A DNA fragment, wherein this cytidine is replaced by 5-fluorodeoxycytidine (F) (5'-GGFC-3'), serves as suicide inhibitor recognition sequence (also called mechanism-based inhibitor) for the Hae III methylase and is the location of the covalent bond between DNA and polypeptide. This suicide inhibitor was designed for the elucidation of the three-dimensional structure of M.Hae III methylase in complex with its substrate. (Chen L. et al. (1991) Direct identification of the active-site nucleophile in a DNA (cytosine-5)-methyltransferase. *Biochemistry* 30, 11018). By using oligonucleotides, that contain the modified base 5-fluorodeoxycytidine, the binding sites, that are later used for selection experiments, can be easily incorporated into the DNA by PCR. Oligonucleotides modified with 5-fluorodeoxycytidine are commercially available (Microsynth, Balgach, Switzerland).

The polypeptide to be modified in its properties by the in vitro evolution according to the invention is bound to the C-terminus of the methylase. The fusion protein consists of at least two domains, one of which (Hae III methylase) is responsible for the covalent coupling to the DNA, whereas the other domain determines the properties to be selected for.

A DNA library consisting of linear DNA fragments, that code for M.Hae III fusion proteins is incorporated into a water-in-oil emulsion together with transcription-translation solution and the cofactor S-adenosylmethionine (SAM). The DNA is transcribed in the aqueous compartments and the resulting mRNA is translated. In this way M.Hae III fusion polypeptides are formed, that react with the 5-fluorodeoxycytidine and, thereby, form a covalent bond to the DNA. After extraction of the DNA-methylase fusion protein complexes from the water-in-oil emulsion a selection experiment may be performed in order to either obtain a specifically binding or allosterically effective polypeptide with selected properties.

BRIEF DESCRIPTION OF THE DRAWINGS

The present invention will be illustrated with reference to the figures. In this respect.

LIST OF REFERENCE SIGNS

Figure 1:
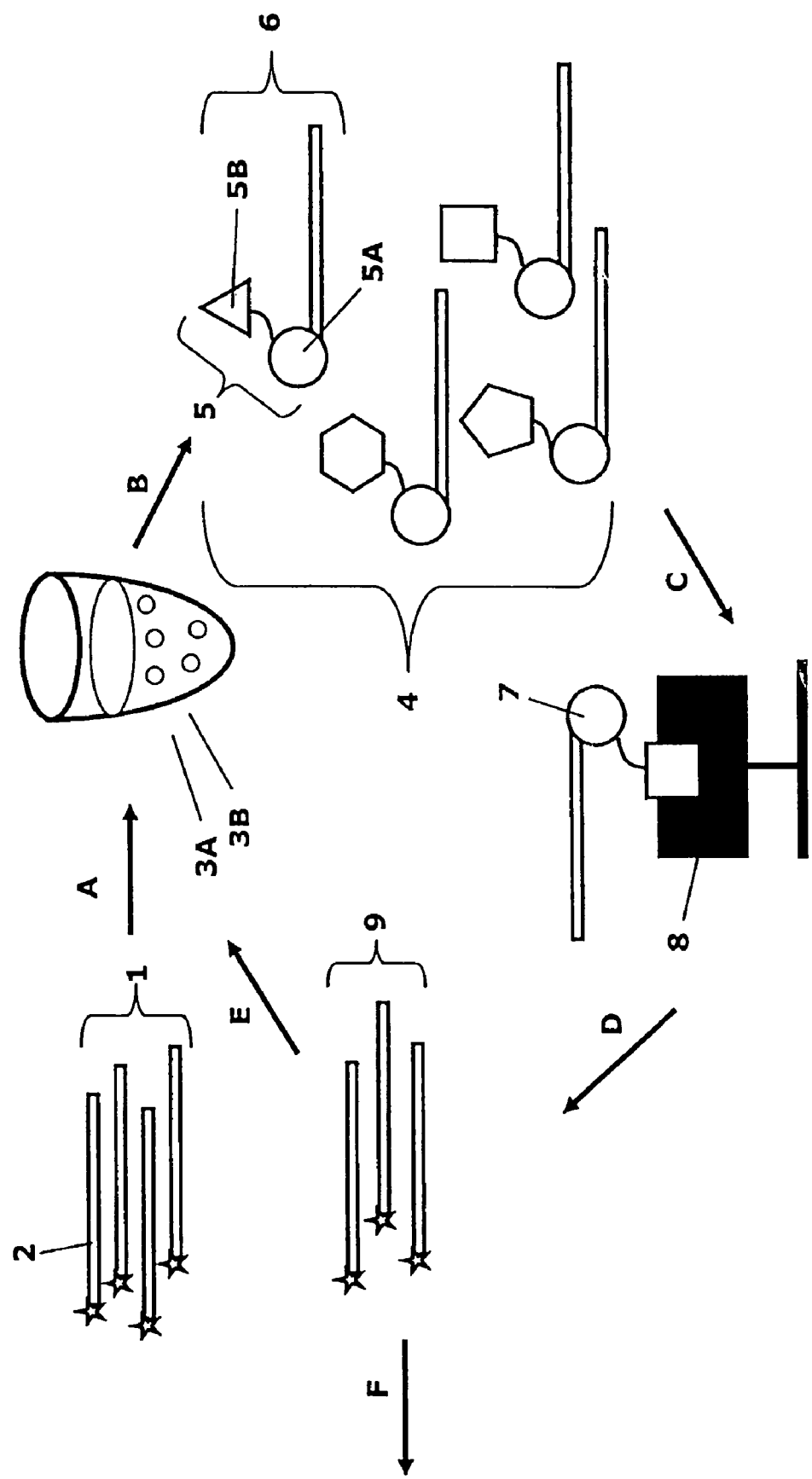
FIG. 1 illustrates a scheme of the selection cycle according to the present invention wherein A represents an encapsulation of the DNA library into microcompartments, B represents an extraction of the emulsion, C represents a selection of polypeptides having the best properties, D represents an amplification of the genetic information of the bound polypeptides (PCR), E represents a further selection cycle, F represents cloning of the coded polypeptides, 1 represents a DNA library, 2 represents a DNA molecule, 3A represents a water-in-oil emulsion, 3B represents a water compartment, 4 represents a collection of DNA-polypeptides fusions, polypeptide-DNA complexes, 5 represents fusion polypeptides, 5A represents constant peptide part I, 5B represents variable peptide part II, 6 represents DNA-polypeptide fusion or polypeptide-DNA complex, 7 represents bound polypeptides, 8 represents immobilized target molecules, 9 represents a new collection of genes and * represents a suicide inhibitor.
Figure 2:
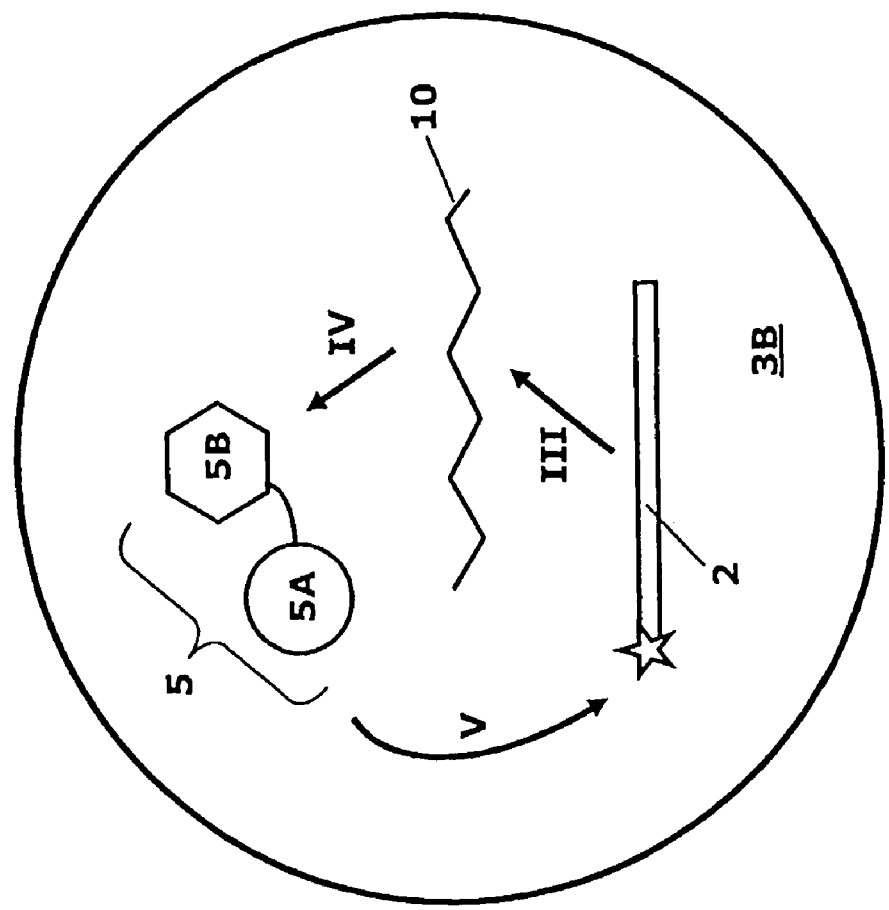
FIG. 2 illustrates a schematic representation of the processes within a micro compartment of a water-in-oil emulsion, wherein 2 represents a DNA molecule, 3B represents a water compartment, 5 represents fusion polypeptides, 5A represents constant peptide part I, 5B represents variable peptide part II, 10 represents mRNA, III represents transcription, IV represents translation, and V represents fusion polypeptide reaction with the suicide inhibitor (*) at or on the DNA molecule.

A Encapsulation of the DNA library into microcompartments
B Extraction of the emulsion
C Selection of polypeptides having the best properties
D Amplification of the genetic information of the bound polypeptides (PCR)
E Further selection cycle
F Cloning of the coded polypeptides
III Transcription
IV Translation
1 DNA library
2 DNA molecule
* Chemical group, suicide inhibitor
3A Water-in-oil emulsion
3B Water compartment
4 Collection of DNA-polypeptides fusions, polypeptide-DNA complexes
5 Fusion polypeptides
5A Constant peptide part I
5B Variable peptide part II
6 DNA-polypeptide fusion or polypeptide-DNA complex
7 Bound polypeptides
8 Immobilized target molecules
9 New collection of genes
10 mRNA In the following the invention will be illustrated in an exemplary non-limiting way with regard to preferred embodiments of the present invention.

EXAMPLES

Example 1

This example illustrates the production of a water-in-oil emulsion with advantageous physical properties.

50 μl of an aqueous phase (ice-cooled transcription/translation mixture (Roche)) with about 100 ng DNA (template for the expression, the amount may be varied) and 80 μM S-adenosylmethionine were added to 950 μl of an ice-cooled oil phase (mineral oil (Sigma, M-5904), 4.5% (v/v) Span 80 (Fluka) and 0.5% (v/v) Tween 80 (Fluka), freshly prepared).

The addition was done dropwise in a glass vial for pills (Forma Vitrum AG, 40.0×18.75 mm) over 2 minutes. During the dropwise addition of the aqueous phase in 5 steps of 10 μl each a magnetic stirrer (Heidolph MR 1000) stirred at 2200 rpm (rounds per minute). After addition of the aqueous phase the stirring was continued for another 5 minutes at 2200 rpm to reach the desired size distribution of the compartments.

Figure 3B:
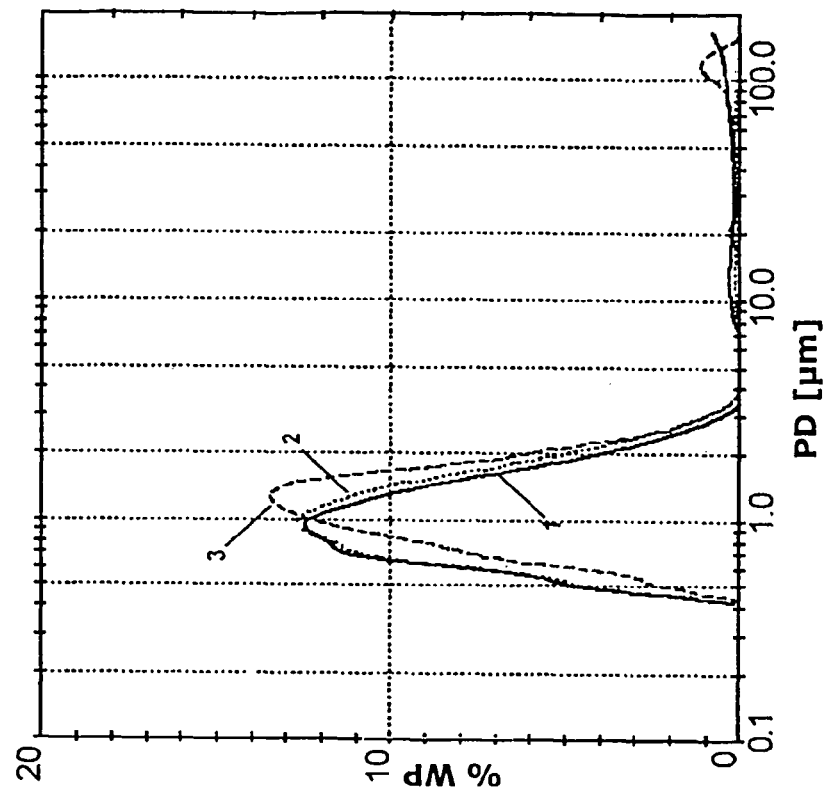
FIG. 3b illustrates the preferred diameter of the water compartments within the range of 1 μm and 2 μm.
Figure 3A:
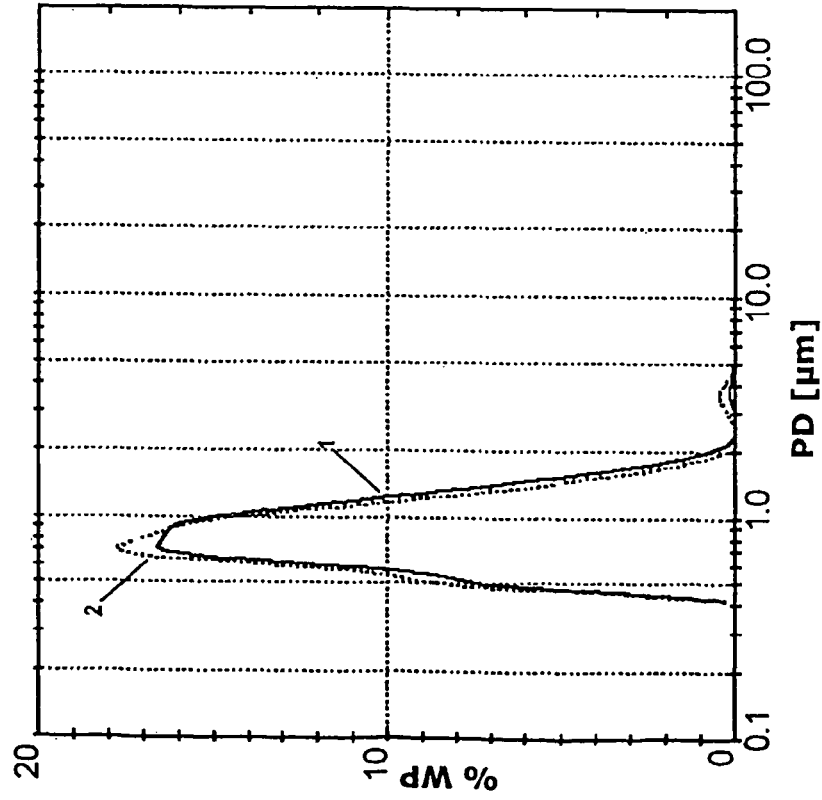
FIG. 3a illustrates the stability of the size distribution of the water compartments of the water-in-oil emulsion.

In FIGS. 3a and 3b the size distributions of the water compartments of a water-in-oil emulsion are illustrated, that were prepared as described above. On the X-axis the diameters of the microcompartments (PD, in μm) are plotted in a logarithmic scale. The values of the Y-axis (% WP) provide for the fraction of the aqueous phase in a mirco-compartment of the corresponding size (WP, in % of the total volume of the aqueous phase).

FIG. 3a illustrates the size distributions of a water-in-oil emulsion at different points in time. An emulsion was prepared and the size distribution of the water compartments was determined directly thereafter by light scattering (time $t_1$=0 h, drawn curve 1). The same measurement was done one more time after the water-in-oil emulsion had been stored for 96 h at room temperature (time $t_2$=96 h, dashed curve 2). The size distributions illustrated by these two curves 1 and 2 do not differ significantly; the emulsions are stable. The size distributions were measured with a Mastersizer X (Malvern Instruments Ltd., UK).

FIG. 3b illustrates the reproducability of three water-in-oil emulsions, that were prepared as described above. The profiles of the size distributions (1, drawn line; 2, dotted line; 3, dashed line) do not differ significantly; the emulsions are reproducable. The size distributions were measured with a Mastersizer X (Malvern Instruments Ltd., UK).

Example 2

This example illustrates the covalent binding of DNA to a polypeptide.

A DNA fragment having a length of 268 bp with a recognition sequence 5'-GGFC-3' was employed for the coupling experiments shown herein (F=5-fluorodeoxycytidine). 2 nM DNA were incubated in reaction buffer (New England Biolabs), 50 mM NaCl, 50 mM Tris-HCl (pH 8.5), 10 mM dithiothreitol, together with M.Hae III (38 nM) and 80 μM S-adenosylmethionine (SAM) (New England Biolabs) at 37° C. for different time periods (15, 30, 60, 120, 180, and 240 min.). The reactions were halted by heating to 70° C. for 15 min. (inactivation of M.Hae III). The samples were analyzed on a denaturing 10% TBE urea gel (Novex). The gel was strained with SYBR green II (Molecular Probes, Oregon, USA). In this way, the single-stranded nucleic acids were rendered visible (see FIG. 4).

Figure 4:
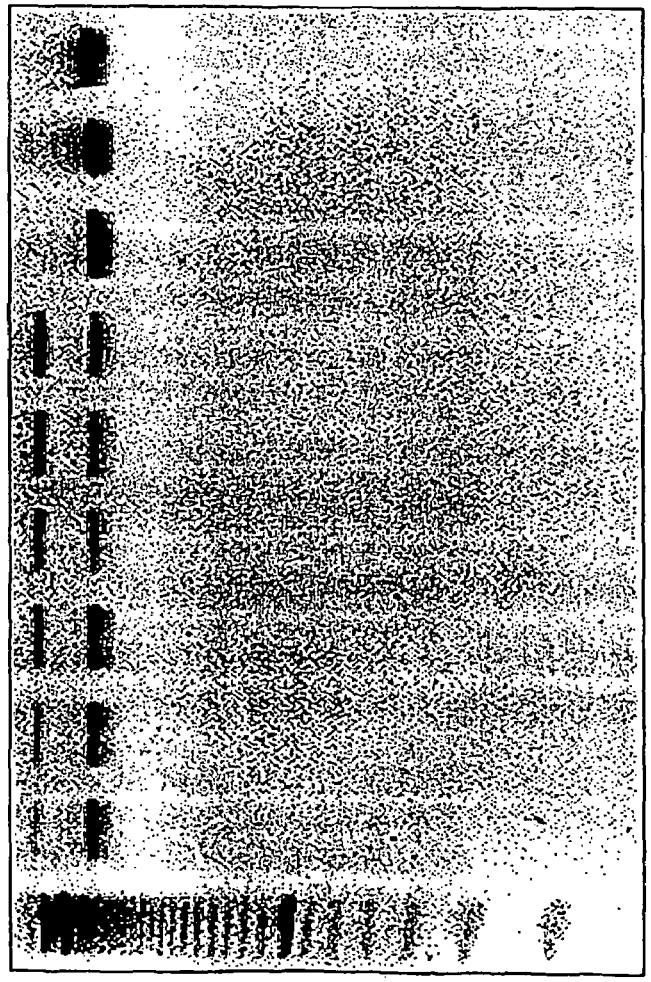
FIG. 4 illustrates the covalent binding of DNA to M.Hae III methylase; wherein lanes 2-7 from left to right the samples are applied with an increasing incubation time (on top of each lane the incubation time is provided from 15'-240'). The lanes X (without cofactors SAM), Y (without M.Hae III methylase) and Z (without the DNA fragment (268 bp))

In the first lane M of the gel shown in FIG. 4 a size marker is applied (10 bp ladder, Invitrogen). In lanes 2-7 from left to right the samples are applied with an increasing incubation time (on top of each lane the incubation time is provided from 15'-240'). The lanes X, Y and Z show three negative controls:
X: Sample without cofactors SAM;
Y: Sample without M.Hae III methylase;
Z: Sample without the DNA fragment (268 bp) used for the reactions.

The use of a denaturing gel and the previous heat treatment to 70° C. ensures that only covalently bonded M.Hae III is associated with DNA. A M.Hae III-bonded DNA migrates on the gel more slowly than an unbound DNA. In FIG. 4 it can be recognized clearly that with an increased incubation time the upper bands gain intensity. This means that more DNA molecules are bound to M.Hae III, when the incubation time increases. After about 2 hours the intensities of the upper and lower bands have about the same strength.

In a double-stranded DNA molecule only one strand contains the suicide inhibitor. If one M.Hae III is covalently bound to each recognition sequence 5'-GGFC-3'—and, therefore, to each double-stranded DNA, then half of all DNA single strands are bound to the methylase. Because the upper and the lower bands of the gels show the same intensity, there are the same numbers of non-modified as well as M.Hae III-associated single strands. This means, that the binding occurred quantitatively after about 2 hours.

Example 3

In this example M.Hae III fusion proteins are expressed in vitro.

For the expression of M.Hae III fusion proteins a commercially available transcription-/translation system was employed (RTS *E. coli* HY Kit, Roche Applied Science, Switzerland). In order to express a gene with this in vitro system, regulatory DNA sequences must be added to the 5'- and the 3'-ends. This is done by overlapping PCR (PCR assembly). The sequences are commercially available (RTS *E. coli* Linear Template Generation Set, His-tag, Roche Applied Science, Switzerland).

In order to introduce the suicide inhibitor 5'-GGFC-3' into the DNA by PCR, a further PCR was performed with the DNA fragments obtained by the Linear Template Generation Set. As primers (oligonucleotides) Lin ext ba and Hae sub fo were used. Hae sub fo has a recognition sequence for the Hae III methylase with a 5'-fluorodeoxycytidine (suicide inhibitor). The PCR was performed with the following temperature program:

94° C. (3 min.)→[94° C. (1 min.)→58° C.(1 min.)→72° C. (3 min.)]$_{30\ cycles}$→72° C. (5 min.)→4° C.

The PCR products were purified with the QIAquick PCR Purification Kit of Qiagen.

Sequence of Lin ext ba:

(SEQ ID NO. 1)
5'- GAT GCC GGC CAC GAT GCG TCC GGC -3'

Sequence of Hae sub fo:

(SEQ ID NO. 2)
5'- C GTC ATG GFC TAT GCG GGC GAC CAC ACC CGT CCT GTG GAT -3'

DNA templates coding for M.Hae III-His tag, M.Hae III-Flag tag, M.Hae III-Calmodulin-His tag and M.Hae III-ED-B-His tag were prepared the same way (ED-B: extra domain B of fibronectin). The fusions to Hae III methylase were all bound to its C-terminus. The fusionsproteins were expressed in free solution and in emulsion.

Expression in Free Solution:
200 ng of each DNA template were incubated in 25 µl in vitro transcriptions-/translation mixture (Roche Applied Science) for 3 h at 30° C.

Expression in Emulsion:
300 ng of each DNA template were incubated in ice-cooled 50 µl in vitro transcriptions-/translation mixture (Roche Applied Science). The water-in-oil emulsions were prepared as described above. The finished emulsions were incubated for 3 h at 30° C. After expression of the polypeptides and the formation of the DNA-polypeptide fusion complexes the aqueous phase was extracted from the emulsion. The emulsions were centrifuged for 6 minutes at 10.000 rpm, the oil supernatant was removed by suction and 150 µl PBS were added to the sedimented emulsion.

Then, 1 ml ice-cold, water-saturated diethyl ether was added and the sample was well mixed with the vortex. The reaction vial was left standing, so that the organic and aqueous phase could separate. The aqueous phase below the organic phase was then removed by a pipette, filled into a separate reaction vial and incubated for 10 min. at 40° C. in order to evaporate residual diethyl ether.

The expressed amount was analysed by a Western Blot (detection: anti-His-HRP conjugate (Sigma) or: anti-Flag (Sigma) with an anti-mouse-HRP conjugate (Sigma)). By doing so, it was demonstrated that in emulsion about 20 % of the expression yield expected in free solution was obtained. Only the M.Hae III-Calmodulin-His tag fusion protein was unable to be detected in the expression in the emulsion. No fragments of the fusion proteins were detected, what allows for concluding a low protease activity.

Also, the methylase activity of the expressed fusion proteins was analyzed. By methylating the target sequence 5'-GCGGCCGC-3' a DNA fragment can be protected from digestion with the restriction enzyme Not I. When a DNA fragment containing a Not I cleavage site is incubated with M.Hae III fusion proteins, then it cannot be cleaved by Not I afterwards.

Transcription-/translation solutions, wherein a M.Hae III fusion protein had been expressed, were incubated with a DNA fragment containing Not I. Then it was investigated, whether the DNA fragments can still be cleaved with Not I. In all cases investigated the expressed proteins were active. One exception was the M.Hae III-Calmodulin-His tag fusion protein, that was expressed in water-in-oil, that protected the DNA with the Not I restriction site by only 50%. This allows for concluding a low expression level.

Example 4

This example shows the assortment, here selection, of DNA fragments by Ni-affinity chromatography, that are bound to M.Hae III-His tag. When the same DNA fragment is not coupled to an M.Hae III-His tag protein, it is not selected.

At first, the DNA was coupled to the M.Hae III-His tag protein by incubating a DNA template coding for M.Hae III with recombinantly produced M.Hae III-His tag.

2 nM of DNA were incubated in reaction buffer (New England Biolabs, 50 mM NaCl, 50 mM Tris-HCl (pH 8.5), 10 mM dithiothreitol) together with 350 ng M.Hae III-His tag and 80 µM S-adenosylmethionin for 1½ hours at 37° C. (total reaction volume: 30 µl). For the negative control M.Hae III-His tag was excluded.

After the incubation 50 µl buffer A (50 mM NaH$_2$PO$_4$, 300 mM NaCl, 10 mM imidazole, 0.1% Tween 20 (Fluka) pH=8.0) were added.

20 µl Ni-NTA magnetic agarose beads (Qiagen, Cat. No. 36111) were added and the sample was incubated for 1 h at room temperature.

The magnetic Ni-NTA agarose beads were washed four times with 100 µl Puffer B (50 mM NaH$_2$PO$_4$, 300 mM NaCl, 20 mM imidazole, 0.1% Tween 20, pH 8.0) by a Magnetic Separator (MPC-S, Dynal, Norway).

After the last washing step the Ni-NTA magnetic agarose beads were resuspended in 100 µl sterile water.

With 1 µl of the washed nickel beads the amount of the remaining DNA was analyzed by quantitative PCR (Wang A. M. et al. (1989) Quantitation of mRNA by the polymerase chain reaction. *Proc. Natl. Acad. Sci.* 86, 9717). In this PCR only the last 331 base pairs at the 3'-end of the template were amplified. As primers the oligonucleotides Hae end ba (downstream) and Hae sub fo short 2 (upstream) were used. As competitor DNA the template was employed (0.1 pM), that coded for the M.Hae III-ED-B-His tag fusion protein. With the above primers a DNA fragment of 577 bp in length is amplified starting from this template. After the amplification of the selected nucleic acids the samples were placed on an agarose gel (1.4%).

Figure 5:
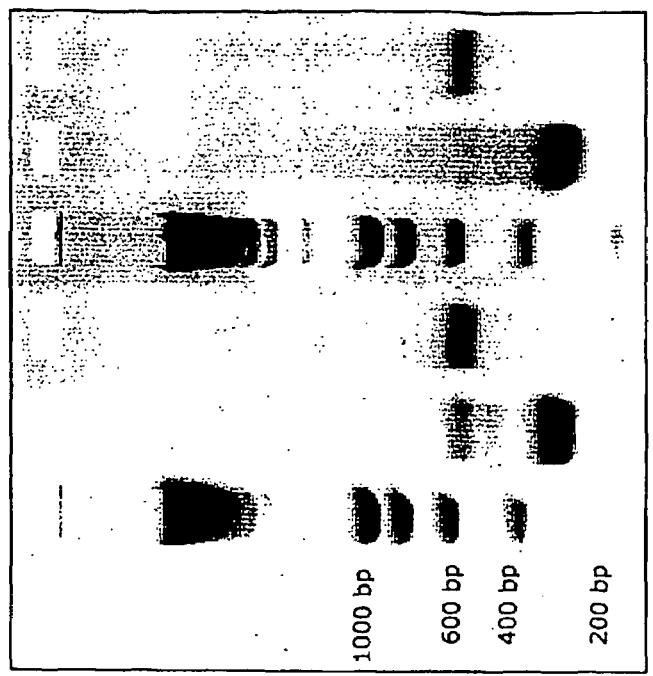
FIG. 5 illustrates the choice, here selection, of M.Hae III-His-tag-DNA-complexes by means of Ni-affinity chromatography.

The agarose gel is shown in FIG. 5. In lanes 1 and 4 a size marker is loaded (Smart Ladder, Eurogentech). The band closely below the 600 bp label is the DNA fragment, that was added to the PCR as a competitor. The lower band is the 331 bp DNA fragment, that had been incubated with the enzyme M.Hae III. In lane 2 the experiment was apllied, in lane 3 the negative control without M.Hae-His tag. In lane 5 0.1 pM of the 331 bp DNA molecule was added to the PCR solution for quantitative comparison. Lane 6 shows the result of the PCR with competitor DNA (negative control) only.

Example 5

Expression of M.Hae-His tag and M.Hae-Flag tag fusion polypeptides in vitro and subsequent assortment, here selection, by affinity chromatography.

The genes coding for M.Hae III-His tag (I) and M.Hae III-Flag (II) tag were cloned according to routine methods for the skilled person into the plasmid pIVEX 2.3d (Roche Applied Science, Switzerland). 500 ng each of both plasmids were incubated in 25 µl transcriptions/translation mixture (Roche Applied Science, Switzerland) for 2 h at 30° C. each. Additionally, linear DNA template (50 ng each) coding for M.Hae III-His tag (III) and M.Hae III-Flag tag (IV) was also incubated in 25 µl transcriptions/translation mixture for 2 h at 30° C. The expression of the polypeptides was audited by Western Blot (see Example 3, too).

To samples I to IV 50 µl buffer A (50 mM NaH$_2$PO$_4$, 300 mM NaCl, 10 mM imidazole, 0.1% Tween 20 (Fluka) pH 8.0) were added. 20 µl Ni-NTA magnetic agarose beads (Qiagen, Cat. No. 36111) were added and the samples were incubated for 1 h at room temperature. The magnetic Ni-NTA agarose beads were washed six times with 100 µl buffer B (50 mM NaH$_2$PO$_4$, 300 mM NaCl, 20 mM imidazole, 0.1% Tween 20, pH 8.0) by f a Magnetic Separator (MPC-S, Dynal, Norway). After the last washing step the Ni-NTA magnetic agarose beads were again suspended in 100 µl PBS. With 1 µl of the washed nickel beads the amount of the remaining DNA was analyzed by PCR.

For the PCR the primers M.Hae Nco Ba (downstream) and M.Hae Xho His fo (upstream) were used. With these primers a DNA fragment of 1020 bp was amplified. For the PCR the following temperature programm was used:

94° C. (3 min.)→[94° C. (1 min.)→55° C. (1 min.)→72° C. (90 sec.)]$_{25\ cycles}$→72° C. (3 min.)→4° C.

Figure 6A:
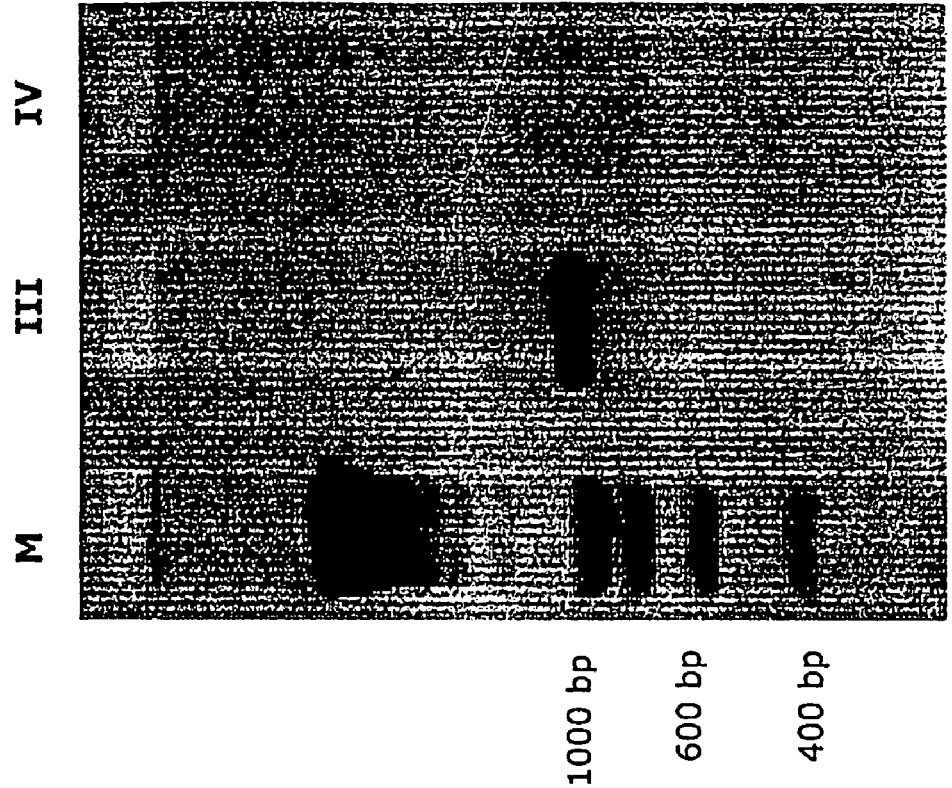
FIG. 6a/b illustrates the assortment, here selection, by Ni-affinity chromatography of M.Hae III-His-tag and M.Hae III-Flag-tag DNA complexes after in vitro expression of the polypeptides and formation of the corresponding DNA-M.Hae III complexes.
Figure 6B:
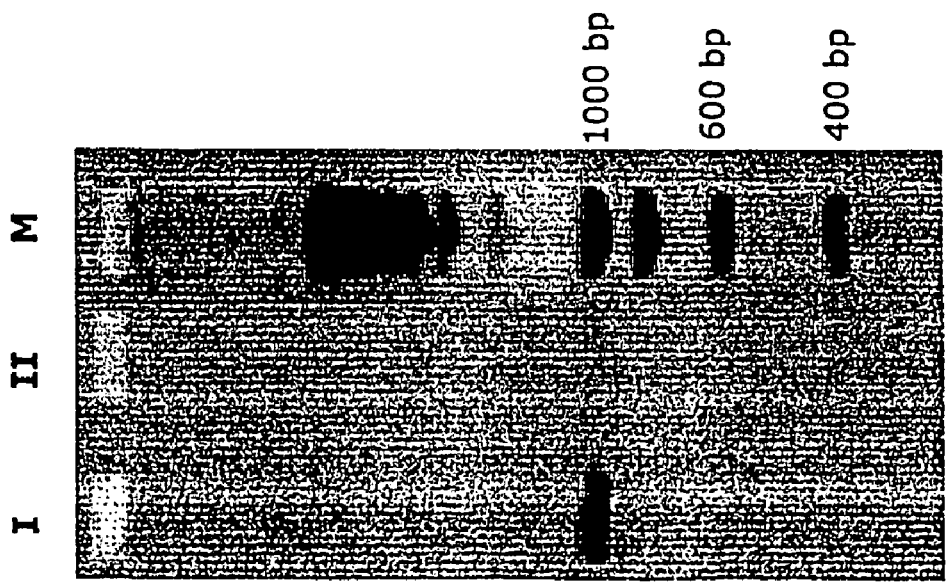

The PCR samples I to IV were applied to an agarose gel (1.4%) for analysis (see FIGS. 6a and 6b).

FIG. 6a illustrates the selection experiment with the plasmid DNA as template for the in vitro transcription/translation. In the lane on the outer right side (M) 5 µl of a size marker were loaded (Smart Ladder, Eurogentech). In the first lane (I) on the left the sample was loaded, wherein the plasmid coding for M.Hae III-Flag tag had been employed the in vitro transcription/translation. In the middle lane (II) the sample was loaded, wherein the plasmid coding for M.Hae III-Flag, tag had been employed for the in vitro transcription/translation.

FIG. 6b illustrates the assortment—, i.e. selection experiment, using the linear DNA as template for the in vitro transcription/translation. In the lane on the outer left (M) 5 µl of a size marker were loaded (Smart Ladder, Eurogentech). In the middle lane (III) the sample was loaded, wherein the linear DNA coding for M.Hae III-His tag had been employed for the in vitro transcription/translation. In the right lane (IV) the sample was loaded, wherein the linear DNA coding for M.Hae III-Flag tag had been employed for the in vitro transcription/translation.

From the intensities of the DNA bands on the agarose gel of FIG. 6a and FIG. 6b it can be clearly recognized that DNA coupled to M.Hae III-His tag fusion polypeptide was selected by Ni affinity chromatography and amplified, whereas DNA bound to M.Hae III-Flag tag fusion polypeptide did not survive the selection cycle.

Example 6

In the following linear DNA molecules are selected in an exemplary manner based on the binding properties of the proteins coded by these.

For this purpose a DNA template was produced that coded for the fusion protein M.Hae III-Calmodulin. This DNA template was prepared in the same way as in Example 3.

An in vitro transcription/translation mixture was prepared according to the instructions of the manufacturer of the kit (RTS E. coli HY Kit, Roche Applied Sciences) while cooled on ice. 40 µl transcription/translation mixture, 5 µl S-adenosylmethionine (end concentration 80 µM), 100 ng M.Hae III-Calmodulin DNA template (about 5×10$^{10}$ molecules) and water were added in such a manner that a volume of 50 µl in total was obtained. The DNA was added shortly before the emulsifying. For the preparation of the emulsion the aqueous phase was added stepwise (5×10 µl over 2 min.) to 950 µl of the oil phase, as it is described in Example 1.

For the expression of the proteins and the production of the covalent protein-DNA complexes the samples were incubated at 30° C. for 150 min. Subsequently, the aqueous phase containing the DNA-protein fusions was extracted from the emulsion as follows:

The samples were centrifuged for 10 min, at 7,000 rpm, whereafter the water compartments sedimented at the bottom of the reaction vials. The supernatant (oil phase) was suctioned off and 150 µl buffer were added (buffer consisting of: TBS (Tris-buffered saline) with 1 mM CaCl$_2$ (=TBSC), pH 7.4, 5 µM biotinylated double-stranded DNA fragments for blocking the magnetic beads employed later on [5'-biotin-GGA GCT TCT GCA TTC TGT GTG CTG-3' (SEQ ID NO. 3 (Qiagen)], 1 µM competing double-stranded DNA fragments [5'-ATC TAA GGC CAA TGT ACT AGA CGG CCA TTC CAG ATG CAG GCC AAG CGT ACA TAC GGC CTA GCT AAA TCA AGG CCG TAT CGT-3' (SEQ ID NO. 4), substrate sequence for M.Hae III in bold letters (Qiagen)])

followed by 1 ml diethyl ether. Subsequently, the sample was shaken with a vortex for 2×10 sec. After the separation of the water phase and the oil phase the aqueous phase lying below was removed with a pipette and dried in a 24-microtiter plate for 10 min., so that the remaining diethyl ether was allowed to evaporate completely.

During the extraction of the aqueous phase 25 µl magnetic beads coated with streptavidine (Dynabeads, Dynal, Norway) were incubated with biotinylated, Calmodulin-binding peptide (400 nM, biotin-CAAARWKKAFIAVSAANRFKKIS (SEQ ID NO. 5) (Montigiani et al., 1996) or with biotinylated anti-Flag antibody M2 (2 µl/50 µl beads, M2 antibody, Sigma-Aldrich) for 15 min. The Calmodulin-binding peptide was used to select the M.Hae III-Calmodulin-DNA fusions located in the aqueous phase of the emulsion, whereas the anti-Flag antibody was employed as a negative control. After the incubation of the magnetic beads with peptides or antibodies these were washed once with TBSC 0.1% Tween 20 (Fluka). Subsequently the beads were blocked for 15 min. at room temperature with biotinylated DNA fragments (5 µM) [5'-biotin-GGA GCT TCT GCA TTC TGT GTG CTG-3' (SEQ ID NO. 3) (Qiagen)].

The extracted water phase was divided into two halves and mixed with the above described prepared magnetic beads. One half of the aqueous phase was added to beads coated with Calmodulin-binding peptides, whereas the second half was incubated with beads coated with anti-Flag antibody. Both samples were incubated for 45 min. at room temperature and gently shaken every 10 min.

Then, the magnetic beads were washed six times with 100 µl TBSC 0.1% Tween 20 (Fluka) each and once with 100 µl TBSC by a Magnetic Separator (Dynal, Norway) to remove non-binding DNA-protein fusions from the surface of the magnetic beads. After the washing the magnetic beads were flushed in 100 µl water.

Then, it was assessed how many DNA-M.Hae III-Calmodulin fusion proteins had been selected by binding to magnetic beads coated with Calmodulin-binding peptides or magnetic beads coated with the anti-Flag antibody. This analysis was performed with a method that is routine to the skilled person, i.e. the "Real-time Polymerase Chain Reaction" (real-time PCR) (with the Taq-Man™ System of Applied Biosystems). As a template for the real-time PCR 0.1 µl of 100 µl of all magnetic beads floating in water were used. Each sample was measured three times.

In the sample, wherein magnetic beads coated with Calmodulin-binding peptides had been employed for the selection $7.8 (\pm 1.1) \times 10^5$ DNA molecules were detected on 0.1 µl beads. However, in the negative control with anti-Flag antibody only $6.9 (\pm 1.4) \times 10^2$ DNA molecules were measured (the standard deviation of the results is provided in parenthesis). Consequently, a factor of 1130 more DNA molecules coding for M.Hae III-Calmodulin were selected when the beads were coated with Calmodulin-binding peptides instead of the anti-Flag antibody. The same experiment was also performed with other M.Hae III fusionproteins (with the corresponding antibodies on the magnetic beads) and similar results were obtained. The ratio (experiment/negative control) of the number of selected DNA molecules varied between 557 and 6897.

Example 7

In order to work with libraries with modified (e.g. by adding, substituting, deleting) DNA molecules, it is possible to select with the method described herein only those protein-DNA fusion conjugates from a library that have the desired binding properties.

Therefore, model experiments were performed with mixtures consisting of two different DNA templates. One template coded for the fusion protein M.Hae III-Calmodulin the other for M.Hae III-ED-B. The templates were prepared in the same way as it is described in Example 3. Unless described otherwise, the experiment was performed according to the protocol of Example 6.

To the transcription/translation mixture a mixture of $10^9$ DNA molecules in total was added, wherein a factor of 4200 more DNA molecules coded for the fusion protein M.Hae III-ED-B than for M.Hae III-Calmodulin. The selection experiment was done with magnetic beads that had been coated either with Calmodulin-binding peptides or with anti-Flag antibodies (M2, Sigma-Aldrich). The result of the experiment was evaluated by real-time PCR.

However, the magnetic beads were not used for the real-time PCR directly, but the selected DNA molecules were first amplified in a PCT with the primers Ampl ba (5'-CCC GCG AAA TTA ATA CGA CTC A-3', (SEQ ID NO. 6) Qiagen) and Ampl fo (5'-AAA ACC CCT CAA GAC CCG TT-3', SEQ ID NO. 7) Qiagen). The PCR was performed with the following temperature program:

94° C. (3 min.)→[94° C. (45 sec.)→51° C. (1 min.)→72° C. (100 sec.)]$_{35\ cycles}$→72° C. (3 min.)→4° C.

The ratio of DNA molecules coding for M.Hae III-ED-B and M.Hae III-Calmodulin was measured with real-time PCR [with TaqMan™ samples specific for the gene of ED-B or Calmodulin (Microsynth, Balgach, Switzerland)] after diluting the samples 1:$10^5$ in water. 1 µl of the diluted DNA solutions was employed for the measurements, wherein each measurement was done in triplicate. In the case of the negative control (anti-Flag antibody on the magnetic beads) no DNA molecule were detected that coded for M.Hae III-Calmodulin. In the sample, wherein the magnetic beads with Calmodulin-binding peptides had been used, $1.4 (\pm 0.2) \times 10^6$ DNA molecules coding for M.Hae III-ED-B and $5.1 (\pm 0.7) \times 10^4$ DNA molecules coding for M.Hae III-Calmodulin were detected (the standard deviation of the measurements is provided in parenthesis). Consequently, the ratio of M.Hae III-ED-B and M.Hae III-Calmodulin after the selection was 27. By comparing the ratio of the DNA molecules in the starting mixture (4200) and after the selection (27) this results in an enrichment of 153 for the DNA molecule coding for M.Hae III-Calmodulin.

The invention claimed is:

1. A method for the production and allocation of nucleic acids and the polypeptides coded by these, comprising the following steps: a) the compartmentalisation of nucleic acids together with an in vitro transcription-translation mixture in a water-in-oil emulsion, b) the in vitro expression of fusion polypeptides coded by said nucleic acids in the microcompartments of the water-in-oil emulsion, whereby each nucleic acid is bonded to the fusion polypeptide it codes for, wherein each of the fusion polypeptides comprises at least one constant peptide part I and at least one variable peptide part II, and wherein the fusion polypeptides are covalently bonded to the nucleic acid coding for said fusion polypeptide in step b), and wherein the number of the fusion polypeptides per nucleic acid bonded in this manner is a definable integer.

2. The method according to claim 1, wherein the method additionally comprises the following step: c) the extraction of the fusion polypeptide-nucleic acid complexes prepared in step b) from the water-in-oil emulsion.

3. The method according to claim 2, wherein the method additionally comprises the following step: d) the selection of fusion polypeptide-nucleic acid complexes with desired properties.

4. The method according to claim 3, wherein the method additionally comprises the following step: e) the amplification of the selected nucleic acid molecule.

5. The method according to claim 4, wherein the method additionally comprises the following step: f) the random or directed mutation of one or more nucleotide(s) during or after the amplification of step e).

6. The method according to claim 4 or claim 5, wherein the method additionally comprises the following step: g) the repetition of the methods described in claim 4 or claim 5 once or several times.

7. The method according to claim 1, wherein the nucleic acids are rRNA, mRNA or DNA.

8. The method according to claim 1, wherein the nucleic acid is DNA.

9. The method according to claim 1, wherein the nucleic acids are double-stranded DNA, preferably double-stranded linear DNA.

10. The method according to claim 1, wherein the nucleic acids are chemically modified DNA.

11. The method according to claim 1, wherein each microcompartment of the water-in-oil emulsion does not comprise more than one nucleic acid.

12. The method according to claim 1, wherein the microcompartments prepared in the water-in-oil emulsion have an average diameter of 1 μm to 2 μm.

13. The method according to claim 1, wherein one peptide part I is covalently bonded to one nucleic acid molecule each.

14. The method according to claim 1, wherein the constant peptide part I of the fusion polypeptide is a (cytosine-5-)-methyl transferase.

15. The method according to claim 14, wherein the methyl transferase is selected from the group consisting of M.Hae III, M.Hha I, M.Hpa I, M.Msp I and Alu I.

16. The method according to claim 15, wherein the methyl transferase is Hae III methyl transferase from *haemophilus aegypticus*.

17. The method according to claim 10, wherein the modified nucleic acid comprises the sequence 5'-GGFC-3' and F is 5-fluorodeoxycytidine.

18. The method according to claim 3, wherein the method additionally comprises the following step: f) the random or directed mutation of one or more nucleotide(s) during or after the selection step d).

* * * * *